United States Patent
Todd

(10) Patent No.: US 8,551,182 B2
(45) Date of Patent: Oct. 8, 2013

(54) RETRIEVABLE URETHRA SPARING PROSTHETIC STENT AND KIDNEY STONE INTERVENTION SYSTEM

(75) Inventor: Michael Edward Todd, Simi Valley, CA (US)

(73) Assignee: UroTech, Inc., Simi Valley, CA (US)

( * ) Notice: Subject to any disclaimer, the term of this patent is extended or adjusted under 35 U.S.C. 154(b) by 217 days.

(21) Appl. No.: 12/430,552

(22) Filed: Apr. 27, 2009

(65) Prior Publication Data

US 2009/0270907 A1 Oct. 29, 2009

Related U.S. Application Data

(60) Provisional application No. 61/048,462, filed on Apr. 28, 2008.

(51) Int. Cl.
*A61F 2/04* (2013.01)

(52) U.S. Cl.
USPC .......................... 623/23.66; 623/23.7; 606/127

(58) Field of Classification Search
USPC ........... 623/1.23, 1.31, 1.32, 1.36, 1.44, 1.46, 623/23.66, 23.7, 1.13, 23.64, 23.65, 23.67, 623/23.68, 23.69; 606/127
See application file for complete search history.

(56) References Cited

U.S. PATENT DOCUMENTS

| | | | |
|---|---|---|---|
| 3,472,230 A | 10/1969 | Fogarty | |
| 4,790,812 A | 12/1988 | Hawkins, Jr. et al. | |
| 5,772,644 A | 6/1998 | Bark et al. | |
| 6,389,609 B1 | 5/2002 | Andritz | |
| 6,517,531 B2 | 2/2003 | Liu et al. | |
| 6,780,193 B2 | 8/2004 | Leslie et al. | |
| 2006/0173525 A1* | 8/2006 | Behl et al. | 623/1.11 |
| 2006/0206213 A1* | 9/2006 | Hammond et al. | 623/23.66 |
| 2007/0203559 A1* | 8/2007 | Freudenthal et al. | 623/1.3 |

OTHER PUBLICATIONS

Litwin MS, Saigal CS. Introduction. In: Litwin MS, Saigal CS, editors. Urologic Diseases in America. DHHS, PHS, NIH, NIDDK. Washington, DC: GPO; 2007. NIH publication 07-5512:3-7, see http://kidney.niddk.nih.gov/kudiseases/ pubs/kustats/, last accessed Feb. 18, 2009.

* cited by examiner

*Primary Examiner* — Thomas McEvoy
(74) *Attorney, Agent, or Firm* — SoCal IP Law Group LLP; Guy L. Cumberbatch; Steven C. Sereboff

(57) ABSTRACT

The present invention provides devices, a system, and a method for removing kidney stones from the urinary system of a patient with reduced pain and expenses. The system includes expandable, elongated balloon sheaths that deliver and retrieve forceps and a urethral sparing prosthetic stent. The stent is reconstrainable with interwoven nylon strands that are strategically positioned amongst the struts to ensure smooth collapse for removal. An atraumatic coating of PTFE or PET lining on the stent extends from the struts through the tip of the penis to assist patients in passing stones while the stent is in place at the bladder neck. The stent can stay in place for several days while permitting urine drainage. The basket-shaped forceps device has multiple curved, rigid arms to dilate the urethra and capture occluded or embedded stones with a built-in camera. The method is for removing stones through a protected urethral canal.

15 Claims, 12 Drawing Sheets

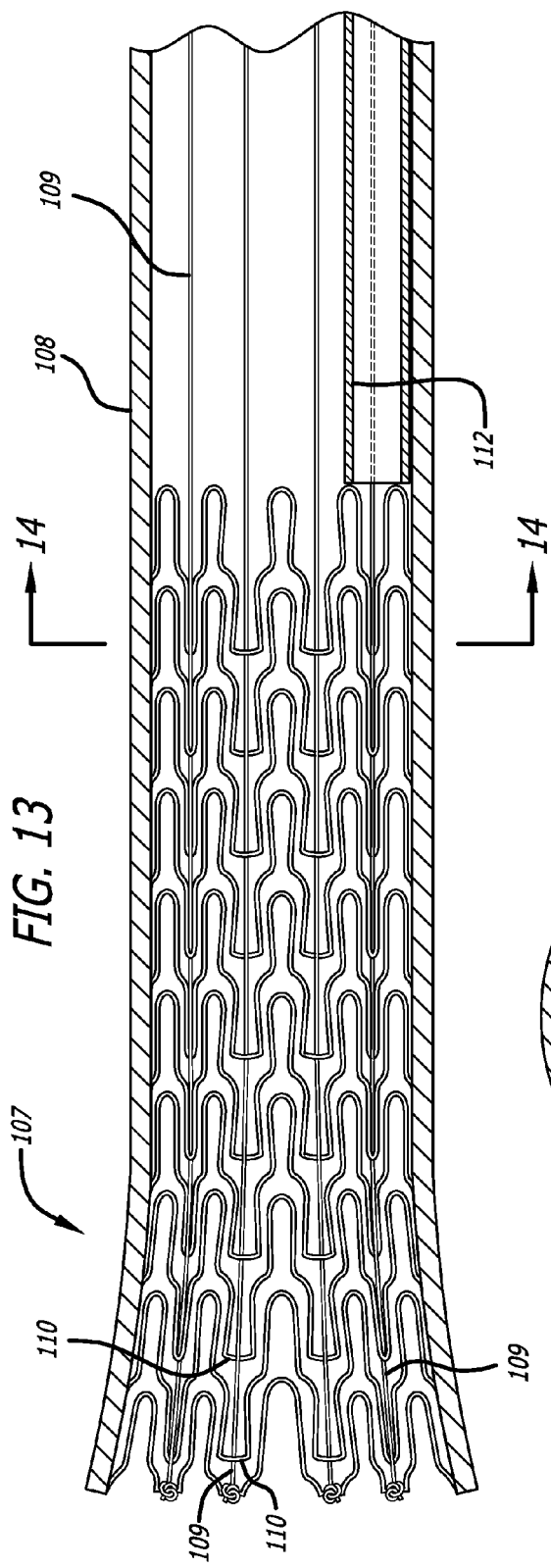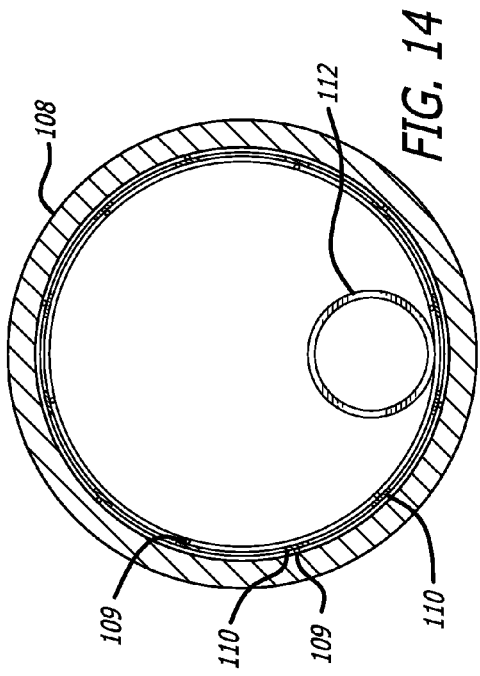

RETRIEVABLE URETHRA SPARING PROSTHETIC STENT AND KIDNEY STONE INTERVENTION SYSTEM

BACKGROUND OF THE INVENTION

1. Field of the Invention

The invention relates to medical devices to assist an individual in passing kidney stones while preserving the urethral lining through which the stones pass.

2. Description of the Related Art

Kidney stones are one of the most painful urologic disorders and yet also one of the most common. In the year 2000 in the United States there were roughly 2.7 million doctor visits and outpatient hospital visits by adults aged 20 or older with "calculus of kidney and ureters" as a listed diagnosis (Litwin M S, Saigal C S. Introduction. In: Litwin M S, Saigal C S, editors. *Urologic Diseases in America*. DHHS, PHS, NIH, NIDDK. Washington, D.C.: GPO; 2007. NIH publication 07-5512:3-7). Men tend to be afflicted with kidney stones more than woman and the risk of a man developing kidney stones rises at forty years of age.

A stone is essentially a hard mass of crystals that precipitate out of and separate from the urine to build up on the inner surfaces of the kidney. In healthy individuals, chemicals in the urine inhibit the crystals from forming. In afflicted individuals, these chemical inhibitors do not work properly.

The stones are made up of various combinations of chemicals but the most common constituents are calcium with oxalate or phosphate. Struvite stones are a less common variety caused by a urinary tract infection. Bacteria such as *proteus* and *klebsiella* associated with urinary tract infections produce the ammonia which is a precursor to struvite stone formation. Even less common varieties of stones are uric acid stones and cystine stones. Uric acid stones result from a low volume of urine with a low pH. They are more likely to occur in chemotherapy patients, dehydrated individuals, and those with inflammatory bowel disorders. The formation of cystine stones is associated with urine with a high pH and a rare disease called Cystinuria most common in children and young adults.

Urolithiasis is the medical term used to describe stones occurring in the urinary tract while nephrolithiasis describes stones occurring in the kidneys. More specific terms exist to identify the position of the stone within the urinary tract (comprising two ureters, the bladder, and the urethra). For example, ureterolithiasis is used to describe kidney stones specifically in the ureter. The ureter is made up of two narrow tubes that carry urine from the kidney to the bladder. From the bladder, urine exits the body via the urethra.

There is a paucity of treatment options for individuals afflicted with kidney stones. Chemical treatment options are generally impractical because acidic chemicals powerful enough to dissolve the stones also severely damage and are toxic in the urinary system in which the stones reside.

Some of the most recent kidney stone removal assistance devices comprise wires that branch from strands into filaments to create a multi-filament collector. Stones enter the device at the proximal end through gaps between the strands (wires) and are then retained by the multi-filaments distal to the spaced strands. In contrast, according to the basket forceps design of the present invention stones enter at the distal end as the arms open and dilate the urethra to release the stone into the forceps grasp for removal. Once grasped, the stone(s) are retained at the proximal end (bottom of the "basket") as the arms close. United States Patent No. (hereinafter "USP") U.S. Pat. No. 6,780,193 ("Surgical extractor" by Leslie, et al.) assigned to Boston Scientific Corporation discloses such a device with wires, strands, and filaments. Since the wires that form spaced strands must be limited in thickness and number to permit stones to enter between them, they may not be strong enough to provide a retraction function as do the rigid arms of the basket forceps of the present invention.

Other variations of the branched wire concept involve strands with distal ends that connect to a web-like fabric porous material instead of branching into multiple filaments. For, example U.S. Pat. No. 3,472,230 ("Umbrella catheter" by Thomas Fogarty and unassigned) discloses an umbrella attached to the distal end of four sliding spring wires. Similarly, U.S. Pat. No. 4,790,812 ("Apparatus and method for removing a target object from a body passageway" by Hawkins, Jr. et al. and unassigned) discloses a parachute basket attached to four helically wound spring wires. Although the dilating basket forceps arms of the present invention could be springing, slidable, and/or helically wound, they can also be stiff and longitudinally fixed in position.

Other devices and techniques to remove kidney stones rely upon fragmentation and aspiration. U.S. Pat. No. 6,517,531 ("Medical suction device" by Liu, et al.) assigned to Scimed Life Systems, Inc. describes a dual-lumen elongated member with a first suction lumen for aspiration and a second laser fiber lumen for delivering energy to breakdown larger stones. In contrast, the present invention relies upon mechanical urethral dilation, mechanical agitation, and natural gravitational forces to remove the stones.

Other patents addressing the kidney stone problem have focused on filtering the stones from the urine and securely retaining the stones from the time of collection to the time of lab analysis. U.S. Pat. No. 6,389,609 ("Universal stone catcher urinal system" by Stephen Andritz and unassigned) and U.S. Pat. No. 5,772,644 ("Filter pouch for stone and tissue sample collection" by Bark, et al.) assigned to Microtek Medical, Inc. disclose examples of such a filtration and retention system. These systems have limited utility because they do not address the entire scope of the kidney stone problem. They focus on post-collection sample preservation but do nothing to encourage the release of more difficult stones or alleviate patient pain. A filtration and retention system could be used simultaneously with the present invention and be placed where the stones exit the urethra via the balloon sheath or the retrievable stent's smooth lining.

Accordingly, a system and method is needed to assist individuals in passing kidney stones that: (i) reduces pain, (ii) accelerates passage, (iii) permits urination during the stone collection process, (iv) preserves the urethral lining, (v) has a means to assist with the passage of particularly difficult stones that become lodged deep in the urethral lining, (vi) can remain in place until all stones have passed, and (vii) can be easily removed.

BRIEF SUMMARY OF THE INVENTION

The present invention includes five basic components individually, as a system, and as applied in a method. First, there is a Urethral Balloon Sheath (UBS) to protect the urethral lining during instrument delivery. Second, there is a Urethral Dilating Basket Forceps (UDBF) to clear the urethra of stones prior to insertion of the stent. Third, there is a retrievable Urethral Sparing Prosthetic Stent (USPS) with strands woven into the struts. Fourth, there is an elongated Retrieval Balloon Sheath (RBS) extending to reach the bladder's core to collapse the USPS inside of it. Fifth, there are End Grasping Locking Retrieval Forceps (EGLRF) to initiate the collapse of the USPS within the RBS for a safe removal.

Both sheaths, the UBS and the RBS, are elongated. However, the RBS is longer to reach the bladder's core. The difference between the two sheaths is only the length. The standard UBS only delivers approximately two-third's the length of the RBS to provide access for the basket forceps (during the pre-stent urethral clearance process) and eventual delivery of the USPS. Thus, the standard UBS is for atraumatic delivery of instrumentation only with the instrumentation being the UDBF and the USPS. In contrast, the RBS is for retrieval of instrumentation only with that instrumentation being the USPS. The sheaths (UBS, RBS) are not considered prosthetics, as is the stent (USPS), because they are only in position for a limited time to deliver or retrieve instruments. In contrast, the USPS is in place to protect the urethra for an extended time and is therefore called a prosthetic. Both sheaths can be flat-rolled in a tubular shape for insertion into the urethra.

Before the USPS system is deployed, the urethra and bladder neck should be cleared of stones with the UDBF. The targeted, local, mechanical retraction and dilation provided by the basket forceps permits even large, embedded, and irregularly shaped stones to be removed with minimal pain. Before inserting the UDBF, the UBS should be positioned.

The UBS is inserted up to (just below) the point of the target stone. The UBS is then expanded and dilated in the region of the stone to support the forceps and protect the urethra from instrumentation and/or micro fragments of the stone which could cause pain or irritation. With the standard balloon sheath in position and dilated, the basket forceps can be introduced.

Within the urethra, the Urethral Dilating Basket Forceps (UDBF) remove stones that might otherwise interfere with a smooth entry of the USPS system. At the bladder neck, the UDBF remove stones that would make deployment of the USPS system more difficult. It is important to remove these stones before introduction of the USPS to avoid trapping stones between the luminal wall (of the urethra or bladder neck) and the USPS.

In addition to clearing the urethral pathway to prepare for delivery of the USPS, the UDBF also function to allow normal urination. The UDBF may be used independently without delivery of the USPS following in cases in which there are only a few stones in the urethra blocking urination without stones in the bladder. The USPS is designed to release the stones in the bladder. Patients with occluded urethras can have other injuries that can result from extended urinal occlusion (i.e. urinary tract infections, kidney pain, etc.). The basket forceps provide a quick, easy way to promptly remove stones to immediately improve patient comfort and health.

For use the forceps should be positioned as close to the stone as possible. Once the forceps are in an optimal position, they should be activated. The forceps are activated by opening the multiple curved arms to mechanically dilate the focal point of the urethra at the site of the stone. This sudden mechanical retraction of the urethral wall should induce release of the stone into the forceps basket arms for retrieval. With the curved basket arms in their closed position the stone is secured and may be removed from the body along with the forceps. Outside of the body, the basket arms open to release the stone for biopsy, diagnostics, and/or disposal. The forceps can be reinserted until all stones in the urethra are removed. Alternatively, suction can pull the stone through the shaft (the "throat" or "neck") of the forceps device and outside of the body so that the basket arms of the forceps device are free to dislodge another stone. As another alternative, the basket arms can re-open after dislodging a stone to drop it into the urethral canal (with or without suction therein) so that the stone passes outside of the body through suction or gravity and the forceps are immediately free to dislodge additional stones without being removed from the body and reinserted.

As shown in FIG. 11 and FIG. 12, according to a first of several embodiments, the reconstrainable stent (USPS) 107 is covered with an atraumatic, biocompatible, polytetrafluoroethylene (PTFE) or polyethylene terephthalate (PET) coating 111 to protect the urethra and prevent tissue from infiltrating the stent struts 110. The Urethral Sparing Prosthetic Stent (USPS) 107 also has strategically woven nylon fibers 109 that extend the entire length through the PTFE or PET tubing 108 of the urethral prosthetic, between the inner lining or tubing 108 and the outer coating 111. The woven nylon fibers 109 are also intertwined with the stent struts 110. This woven nylon provides excellent tension if needed to collapse the USPS system for eventual removal. With the stent struts 110 free from ingrown tissue the device can simply and painlessly be removed once all stones have passed from the bladder and exited the USPS. The USPS system coating 111 extends from the bladder's neck down the urethra and beyond the length of the penis.

As shown in FIG. 13 and FIG. 14, according to a second of several embodiments, the reconstrainable stent (USPS) 107 is covered with an atraumatic, biocompatible, polytetrafluoroethylene (PTFE) or polyethylene terephthalate (PET) tubing 108 to protect the urethra and prevent tissue from infiltrating the stent struts 110. The Urethral Sparing Prosthetic Stent (USPS) 107 also has strategically woven nylon fibers 109 that extend the entire length through the PTFE or PET tubing 108 of the urethral prosthetic. The woven nylon fibers 109 are also intertwined with the stent struts 110. This woven nylon provides excellent tension if needed to collapse the USPS system for eventual removal. With the stent struts 110 free from ingrown tissue the device can simply and painlessly be removed once all stones have passed from the bladder and exited the USPS. The USPS system tubing 108 extends from the bladder's neck down the urethra and beyond the length of the penis.

The primary role of the stent system is to maintain an "open" funnel effect at the bladder-urethral junction to ensure that the prosthetic does not migrate or allow any stones to become lodged between the urethral prosthetic and the urethral wall. It is the secondary role of the USPS system to provide outward radial force to mildly dilate the urethra to aid in passing the stones into the system for expulsion. If too much outward radial force is applied it will affect urinary continence. Thus, the outward radial force exerted by the stent at the bladder's neck must strike a balance between sufficient dilation to induce stones within the bladder to fall into the stent without over-dilating such that urine uncontrollably passes as a patient loses control of their bladder.

The USPS system is to be kept in place until ultrasound confirms the bladder is clear of any new or un-passed stones that could re-occlude the urethra or create significant pain and discomfort to the patient to clear without the USPS system. A major advantage of the USPS system is that it can be kept in place overnight even if a patient leaves the medical treatment facility on an outpatient basis.

The UBS delivers the USPS and serves to guard the urethral lining during the delivery process. The USPS is not a balloon. However, the USPS (with the stent portion positioned at the bladder neck) is covered with an extended PTFE or PTE tubing that runs the rest of the length of the urethra (down from the stent portion) and exits the penis. This coated tubing protects the urethral lining from stone abrasion by providing a cushioned and lubricious exit pathway. The stent effectively creates a funnel from the bladder into the coated tubing within the urethra for a smooth exit pathway.

The USPS Retrieval Balloon Sheath (RBS) is longer than a conventional balloon sheath (i.e. the UBS) so that it can reach the core of the bladder. The function of the Retrieval Balloon Sheath (RBS) is to push and release the USPS system into the core of the bladder for removal. The RBS needs to provide enough columnar support to allow the USPS to collapse and miniaturize itself into the RBS for removal, signaling the conclusion of the procedure. The RBS functions in a manner similar to a straw to draw the USPS inside. However, the USPS is drawn back by mechanical force rather than suction force. The mechanical force is applied by pulling the nylon strands of the USPS with the locking retrieval forceps (EGLRF) and maintaining a sturdy position with the RBS at the bladder's core. This pulling of the USPS stent struts via the nylon strands, while stabilizing the RBS, will result in stent collapse due to the nylon's tension to the struts resulting in collapse and miniaturization of the stent (USPS) into the retrieval sheath (RBS).

Painless retrieval of the USPS system is a key feature. As shown in FIG. 11-14, the multiple woven strands 109 attached to the stent 107 are woven into it, including into the struts 110 specifically, and the strands extend out of the body. The strands are sufficiently longer than the urethral canal to ensure the ends do not become lost in the body (i.e. strands from bladder's core to beyond the distal tip of the penis). Removal of the stent is accomplished by pulling the strands 109 to collapse the stent 107 at its struts 110 causing it to re-enter the RBS.

Although the stent provides the primary dilation effect securing the USPS system's placement, the balloon sheaths (UBS and RBS) provide secondary dilation during USPS delivery and retrieval. Both balloon sheaths (UBS and RBS) must be sufficiently rigid and strong. The UBS must be strong enough to withstand delivery of the USPS through it. The RBS must be strong enough to dilate the urethra and push the USPS system into the bladder's core and to permit the collapsed stent to re-enter it without buckling.

A second pair of forceps, micro End Grasping Locking Retrieval Forceps (EGLRF), are used to remove the USPS system after all stones have been cleared from the bladder and urethra. These forceps are used to firmly secure the nylon strands that are interwoven into the stent struts to allow for tension that will collapse the USPS stent back into the RBS to conclude the procedure. The distal tips of the forceps can be activated and locked via a radial thread dial similar to a vice grips. The RBS system is to be loaded over the low profile forceps and into the urethra to be delivered into the bladder's core. The USPS system is pushed into the bladder's core. Once the USPS system is free floating in the bladder the forceps can be pulled back to cause the stent to collapse into the RBS. After the stent is removed the balloon sheath (RBS) should also be deflated and removed.

BRIEF DESCRIPTION OF THE SEVERAL VIEWS OF THE DRAWING

FIG. 13 shows the retrieval strands interwoven with the struts of the Urethral Sparing Prosthetic Stent (USPS) according to a second embodiment.

FIG. 14 is a cross-section of FIG. 13 illustrating the catheter drainage lumen disposed within the tubing lining the stent.

DETAILED DESCRIPTION OF THE INVENTION

Figure 1:
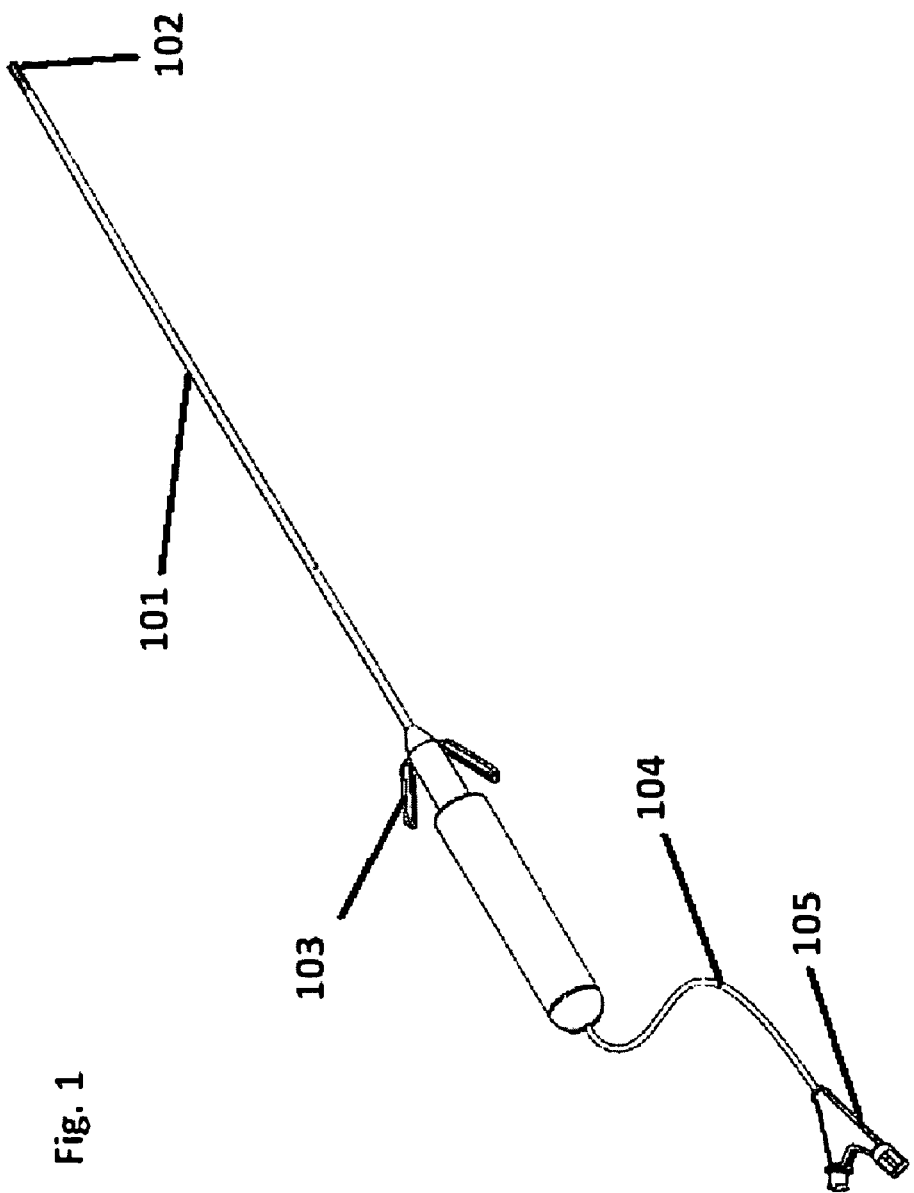
FIG. 1 shows the entire Urethral Dilating Basket Forceps (UDBF) as viewed substantially from the side looking from the proximal end toward the distal end with the connection cable and connector block for a camera system and a light source at the proximal end.

A urethral balloon sheath (UBS) should be inserted to protect the urethral lining during the operation of the basket forceps (UDBF). The basket forceps are used to clear the urethra and the bladder's neck of stones before inserting the USPS system. To ensure that the balloon sheaths (UBS and RBS) are not over-dilated, causing irritation of the urethral lining, the sheaths may be composed partly of non-distensible materials or materials of limited distensibility.

Suitable non-distensible materials include polyester, polyvinylchloride (PVC), polyethylene terephthalate (PET), or polyethylene. Preferably, the outer layer of the balloon that abuts the lumen wall is made of a smooth, elastomeric material, including a silicone elastomer. Optionally, when the balloon is made of multiple layers, a lubricant can be provided in between the layers to reduce sliding frictions and to allow the maintenance of a smooth shape. The diameter of the balloon is around 2 mm to 4 mm during insertion and placement and expands to around 5 mm to 7 mm upon inflation to match the largest non-traumatic diameter of the urethra. In a preferred embodiment, the diameter of the balloon is 3.175 mm during insertion and expands to 5.953-6.350 mm upon inflation. The extent of inflation desired and the exact diameter of the balloon in its inflated condition will depend upon the anatomy of each individual patient, and physician judgment.

In a preferred embodiment, the balloon sheaths (UBS and RBS) are designed to have the structure of a ladder. The steps of the ladder or columns provide radial and/or columnar support. When the balloon is in its deflated, tubular-rolled condition during insertion and placement, the columns provide strength and enhance the pushability of the balloon up the urethra. When the balloon is in its inflated condition, the columns provide radial support and act as buttresses against the urethral wall to ensure it does not collapse or cave-in on the instrument channel created by the balloon sheath. The inflated balloon sheaths serve as a channel to create space for and protect the urethral wall from the forceps, the stones, and the stent.

In a preferred embodiment, the balloon sheaths are inflated with an incompressible coolant fluid (i.e. refridgerated saline solution, nitrous oxide, etc.). The incompressibility of the coolant ensures accurate pressure readings, controlled inflation/deflation, and avoids air bubbles. The cooling nature of the fluid infusion functions to soothe the urethral lining and reduce inflammation.

For deeply embedded stones within the urethra the basket forceps of the present invention should be used prior to insertion of the USPS system. The basket forceps perform the functions of tissue retraction, stone agitation, and stone entrapment. The basket forceps have multiple rounded, rigid arms of sufficient strength to retract tissue and of sufficient density (without too many or too large gaps between adjacent arms) to hold a captured stone inside. According to preferred embodiments, the stone-removing, urethral-dilating basket forceps device has four or five curved arms.

At a proximal handle end of the shaft of the stone-removing, urethral dilating, basket forceps device is a means for opening and closing the multiple curved arms. This means for opening and closing the arms may comprise two squeezable plastic handles of approximately 1" in length that open the curved arms when depressed towards the centerline of the shaft and close the arms to capture a stone upon release. The amount of dilatation depends upon the extent to which the arms are extended outward from the shaft's centerline to put pressure against the urethral walls. In turn, the extent to which the arms are extended outward correlates with how tightly the forceps handles are squeezed together. More pressure applied to squeeze the handles closed translates to more dilatation force from the extended arms and a larger diameter of dilatation. According to a preferred embodiment, the handles open the curved arms of the basket forceps to an outer diameter of around 6 mm when partially depressed and when released the arms close such that their closed position outer diameter is around 4 mm. This degree of extension and retraction of the arms should be sufficient to provide adequate dilatation for most anatomies. However, for those anatomies in which more extensive dilatation is required and/or for larger anatomies the basket forceps arms may extend to 8 mm or more when the handles are completely depressed.

The basket forceps are complimentary to the intervention system and required if stones are present in the bladder neck or urethra so that the USPS can be safely placed. The USPS system is not to be placed until the urethra and bladder neck are clear of stones. When the urethra and bladder neck are clear of stones the USPS can be deployed using a balloon sheath.

In some cases, when there are no stones in the bladder and only embedded stones in the urethral lining, only the dilating basket forceps are needed. In other cases, when there are no stones embedded in the urethral lining but there are stones in the bladder only the USPS is needed. Thus, the dilating basket forceps and the urethral sparing prosthetic stent (USPS) can each be used independently or they can be used together. When they are used together it is critical that the dilating basket forceps are used first. If the physician was to deploy a USPS in a patient with one or more stones in the urethral tract without first removing stones using the basket forceps the patient would experience severe pain as the balloon sheath that delivers the stent and the stent itself expand to compress the stones in the urethral tract more deeply into the urethral lining. Aside from the pain, this also damages the urethral lining. The basket forceps must be used when urethral stones are present because if a balloon sheath and/or stent are placed without them the stones will be pinched between the sheath and/or stent and the urethral wall. This causes pain, increases embedding within the urethral wall, and temporarily buries the urethral stones so that the basket forceps could not access the stones if the forceps were inserted after deployment of the sheath and/or stent (instead of before deployment).

Preferably, the forceps have an atraumatic basket shape with highly curved (rounded) sides. Preferably, the forceps open in a manner similar to slices of a pie expanding radially outward or like a flower blossoming with the distal ends of the petals (the arms) opening. This mechanical opening process must be able to create enough atraumatic dilitation of the urethral lining to release the embedded or occluded stone into the basket for removal. The mechanical opening must also permit eventual placement of the USPS system if the bladder shows additional stones that have yet to enter the urethra.

The forceps are easy to manipulate and to move from stone to stone as each stone is identified. Larger irregular stones can be held within the basket created by the arms of the forceps for removal to ensure that they do not become re-embedded after release, ensuring a smooth exit. However, for smaller embedded stones with smoother surfaces, local agitation via tissue dilation with the rounded arms may be enough to release a stone and to facilitate its exit from the body. Once smaller stones with relatively blunt surfaces are dislodged, they are unlikely to become re-lodged or to cause trauma upon their exit pathway out via the balloon sheath (UBS). These released smaller stones do not need to be carried in the basket of the basket forceps but may instead simply be permitted to fall into the expanded balloon sheath to slide out of the body. Thus, the basket forceps can be used efficiently to agitate and dislodge smaller embedded stones consecutively (via the drop and slide approach) without the need to remove the forceps from the body in between each stone in order to empty the stone from the basket.

For the larger embedded stones and/or for stones with more abrasive surfaces, it may be safer to remove the stones one-by-one and to carry each stone out of the body within the basket created by the curved arms of the forceps. The curved arms form a jail around the stone. Thus, it is the blunt, atraumatic outer surface of the arms that abut and move along the urethral lining (padded by the balloon sheath) rather than the outer surface of the stones. In contrast to the typically rough, jaded edges of a kidney stone, the basket forceps have smooth curved edges. Unaided, large and/or irregularly-shaped kidney stones may cause abrasions, tears, and inflammation of the urethral lining as they pass. However, when stone passage is aided with the basket forceps, the urethral lining and the balloon sheath are both preserved. The ergonomic rounded basket shape and biocompatible material gently dilates the urethra as it moves along for a smooth stone discharge. Even if the basket shape formed by the arms needs to be large (i.e. in order to fit around a large stone), the difference made by the smooth surface and controlled movement of the forceps are significant enough to alleviate pain during passage.

Preferably, the dilating basket forceps are disposable with a visualization and illumination system built into it and/or connectable with it. Part of the visualization and illumination system comprising a fiber optic cable is built into the forceps device and is disposable along with it. Another part of the visualization and illumination system to which the fiber optic cable connects is more expensive, re-usable, and for the most part remains outside the body or near the proximal entrance. The re-usable portion may be a third party endoscopic camera and a third party light source.

The fiber optic cable on the forceps should reach the base of the basket and be configured to act as a camera or to connect to one or more lenses or other optic elements that act as a camera in the base of the basket. The disposable distal elements of the visualization and illumination system in the basket light up and transmit images of a stone for a physician to see before it is approached and embraced with the basket forceps arms. As opposed to other techniques that use a bare (camera-less) grasping instrument and a separate camera on a second instrument shaft and handle, the present invention provides superior visualization with fewer instruments in a constrained space. A camera at the base of the basket forceps provides a viewing angle in which the target (a stone) and grasping arms are naturally aligned. Better visualization enhances stone retrieval accuracy and speed. Fewer instruments improve patient comfort and reduce irritation to the urethral lining.

In an exemplary embodiment, the USPS system is coated with PTFE or PET. The USPS system is inserted into the urethra within a balloon sheath (UBS) after the urethra and the bladder's neck have been cleared of any stones. The distal end of the USPS system should be placed at the bladder's neck. In a preferred embodiment, the strands are made of nylon and there are four of them. However, any biocompatible material that is not biodegradable in the urethra can potentially be used and any number of strands can be present so long as they provide enough angles from which to collapse and minimize the USPS size and provide an equal distributive pulling force to capture the USPS system for a smooth and painless removal.

After the stent is delivered at the bladder's neck, the PTFE or PET prosthetic extends along the entire longitudinal length of the urethra and extends out of the tip of the penis to ensure that stones travel through the USPS system and can easily exit the body without pain or damage to the urethral lining.

Figure 11:
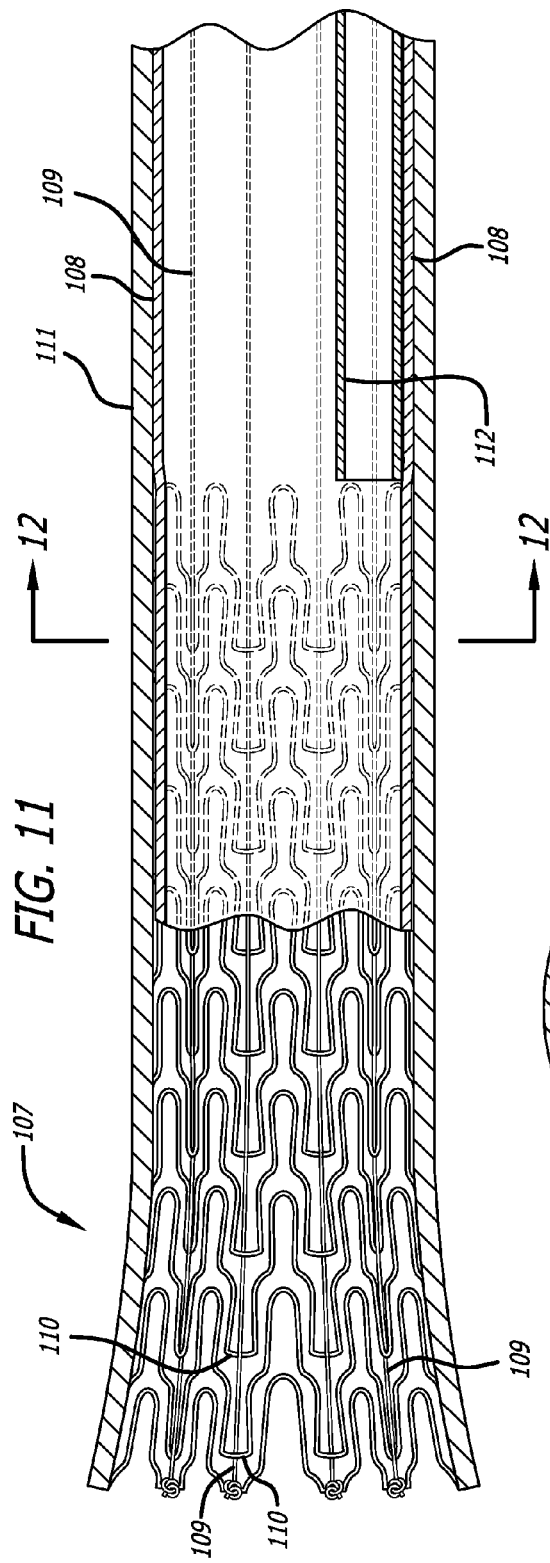
FIG. 11 shows the retrieval strands interwoven with the struts of the Urethral Sparing Prosthetic Stent (USPS) according to a first embodiment.
Figure 12:
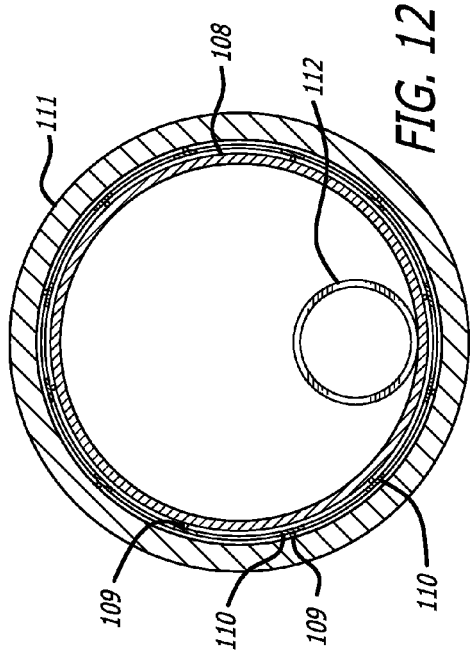
FIG. 12 is a cross-section of FIG. 11 illustrating the catheter drainage lumen disposed within the tubing lining the stent.

An important practical advantage of the USPS system is that it permits urination during the stone collection process. This increases the efficiency of stone removal procedures by allowing the stent and/or sheath to remain in place for longer periods of time. For example, medical personnel can work on difficult embedded stones (with the basket forceps) without frequent interruptions to drain urine. The ability of the USPS system to provide the function of a catheter also increases patient comfort and satisfaction by eliminating the insertion and removal of an independent catheter. In the USPS system the catheter could be incorporated as a separate lumen as part of one of the balloon sheaths and/or as a separate lumen 112 as shown in FIG. 11-14, for example a lumen in the USPS lining or tubing 108 as shown in FIGS. 11 and 12.

With the use of the present invention those individuals afflicted with kidney stones will benefit from less time off of work, a reduced need for pain medication (and its accompanying negative side effects), shorter hospital stays (and reduced hospital bills), and overall increased satisfaction with the ability of a doctor visit to ameliorate their condition.

A review of the illustrations and identification of the reference numerals follows.

FIG. 1 shows the Urethral Dilating Basket Forceps (UDBF) device with the distal arms 102 for expanding the urethral canal and capturing embedded stones, the elongated shaft 101, the handles 103 for opening/closing the arms 102, and a visualization cable 104 and camera connector unit 105.

According a preferred embodiment, when the handles 103 are released and extended outward the arms 102 are close together for initial insertion and then again for enclosing captured stones. Conversely, when the handles 103 are squeezed and brought closer to the body of the instrument the basket forceps arms 102 move apart from one another and open up to receive a stone. However, according to an alternative embodiment the mechanism may be reversed such that the extended handles 103 correspond with open arms 102 and squeezed handles 103 correspond with closed arms 102 (not shown).

The camera connector unit 105 can be adapted to attach to any third party camera system. The connector cable 104 provides a pathway for a fiber optic cable or any other illuminated means for visualizing that transmits recorded visual stimuli from an observation point at the distal end of the instrument (in the center of the basket forceps arms 102) to an external monitor.

Figure 2:
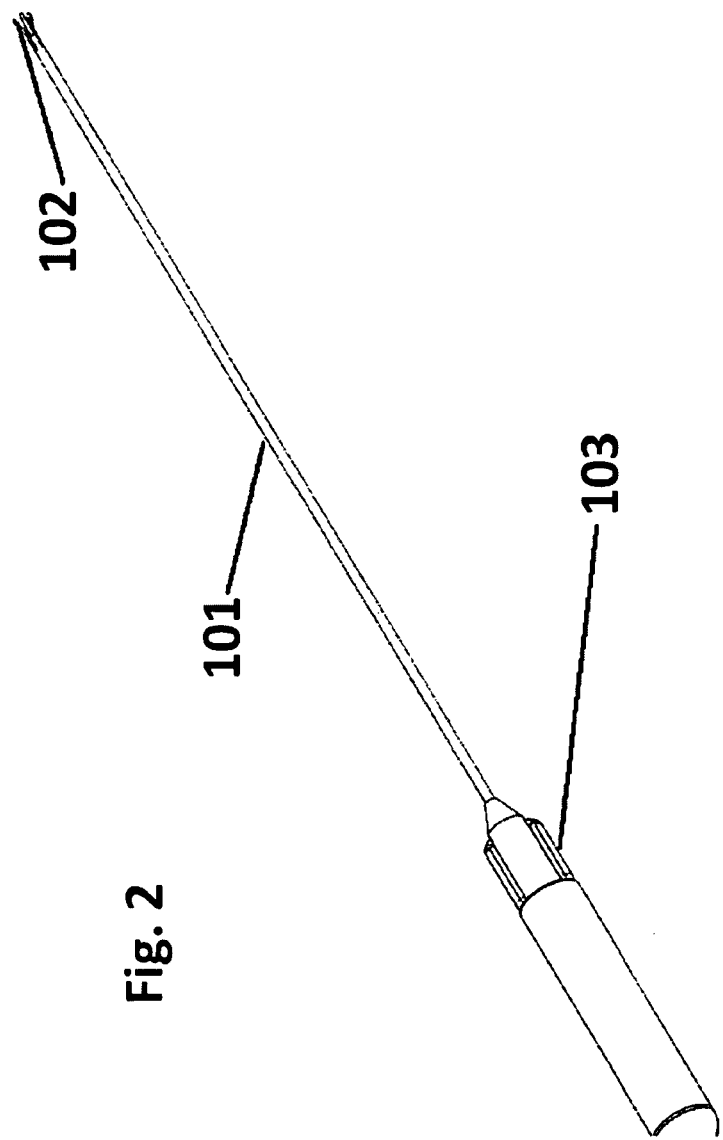
FIG. 2 shows a portion of the Urethral Dilating Basket Forceps (UDBF) as viewed substantially from the side looking from the proximal end toward the distal end (without the proximal connection cable and connector block shown) and with the handles contracted against the body of the instrument placing the distal basket arms in an open extended configuration.

FIG. 2 shows the same UDBF as in FIG. 1 without the connector cable 104 and camera connector unit 105 and in an alternative configuration with the handles 103 squeezed such that the arms 102 have been opened.

Figure 3:
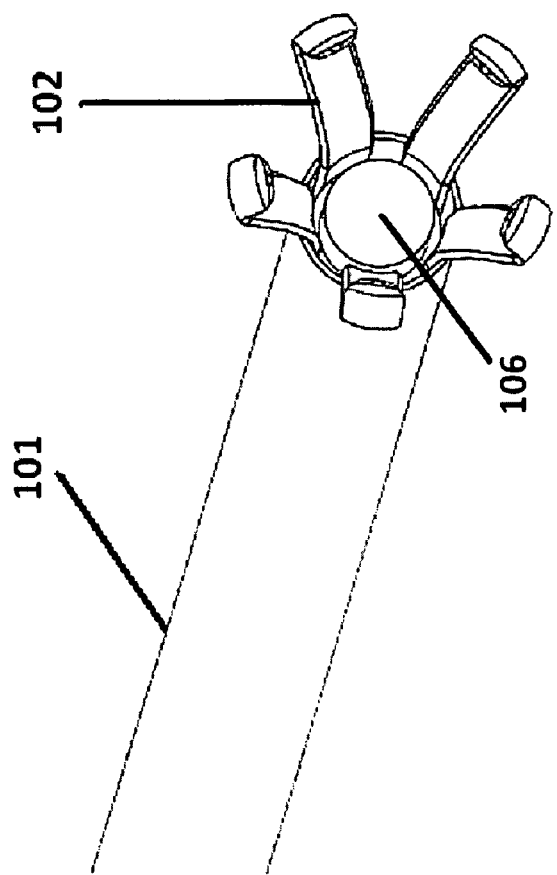
FIG. 3 shows the distal end of the Urethral Dilating Basket Forceps (UDBF) as viewed from the distal end looking into the basket substantially head-on with the five curved arms in an open configuration and an extendable/retractable camera lens at their center.
Figure 4:
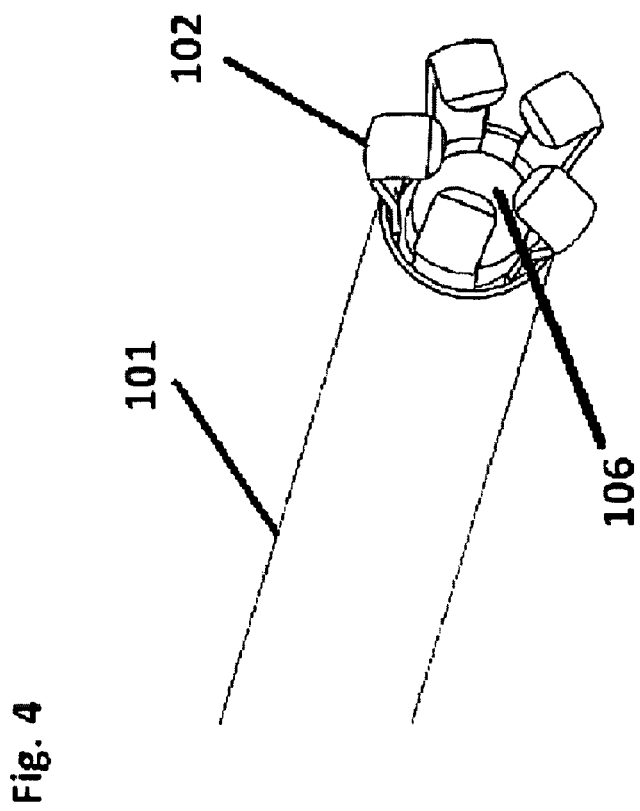
FIG. 4 shows the distal end of the Urethral Dilating Basket Forceps (UDBF) as viewed from the distal end looking into the basket substantially head-on with the five curved arms in a closed configuration and an extendable/retractable camera lens at their center.

FIGS. 3-4 show the distal end of the UDBF viewed approximately head-on with the basket forceps arms 102 surrounding a camera lens 106 in their center and extending from an elongated shaft 101. FIG. 3 shows the arms in the open configuration (i.e. as in FIG. 2 with handles 103 squeezed) while FIG. 4 shows the arms in a closed configuration (i.e. as in FIG. 1 with handles 103 released).

Although all the drawings here show five substantially J-shaped arms any number of arms may be provided with any shape that curves inward to provide maximum stone volume in between the arms and minimum external trauma against a urethral wall. According to a preferred embodiment, the camera lens 106 inside the arms provides 360 degree visualization and can be retracted inward within the housing, extended outward closer to and even past the arms, and optional articulated around and between the arms.

Figure 5:
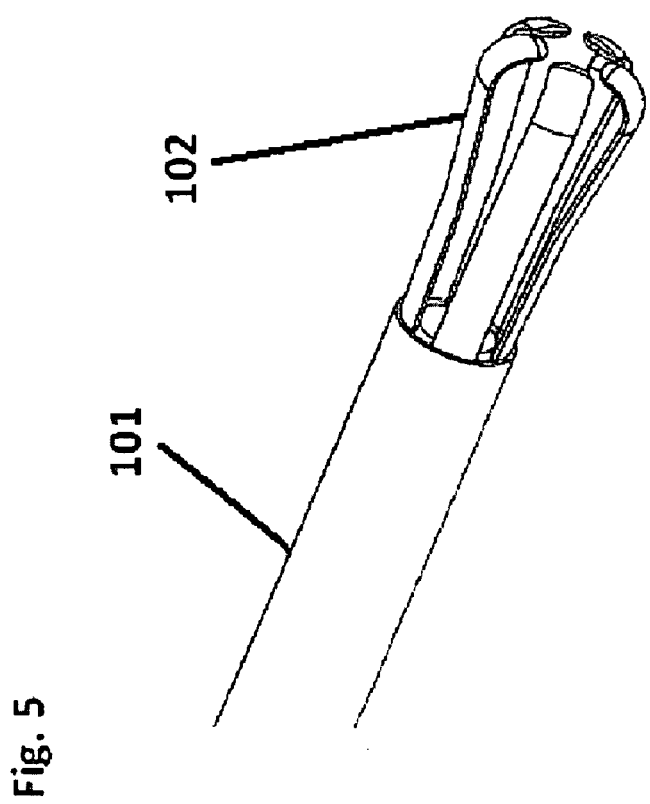
FIG. 5 shows the distal end of the Urethral Dilating Basket Forceps (UDBF) as viewed from the side with the five curved arms in a closed configuration.
Figure 6:
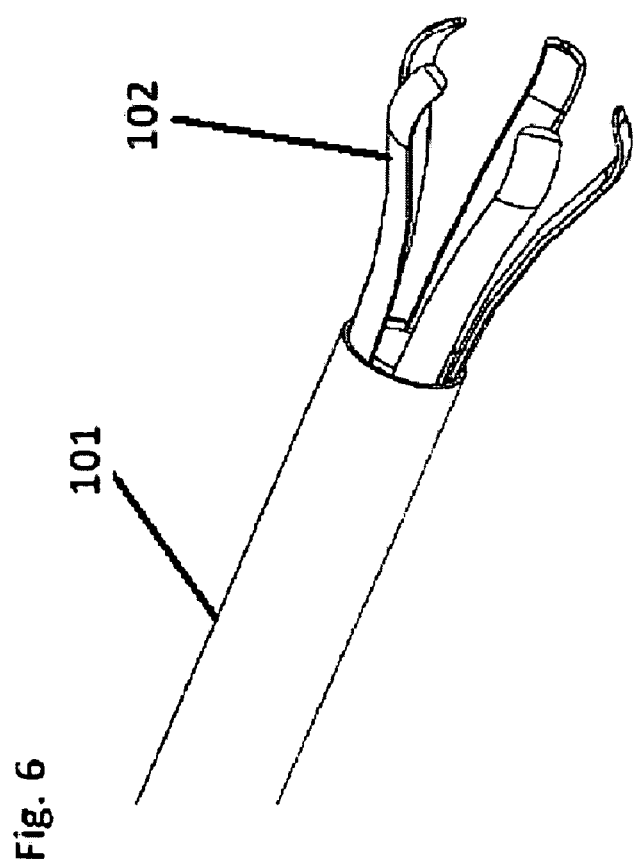
FIG. 6 shows the distal end of the Urethral Dilating Basket Forceps (UDBF) as viewed from the side with the five curved arms in an open configuration.

FIGS. 5-6 show the distal end of the UDBF again from a side view perspective with the arms 102 closed in FIG. 5 and open in FIG. 6.

Figure 7:
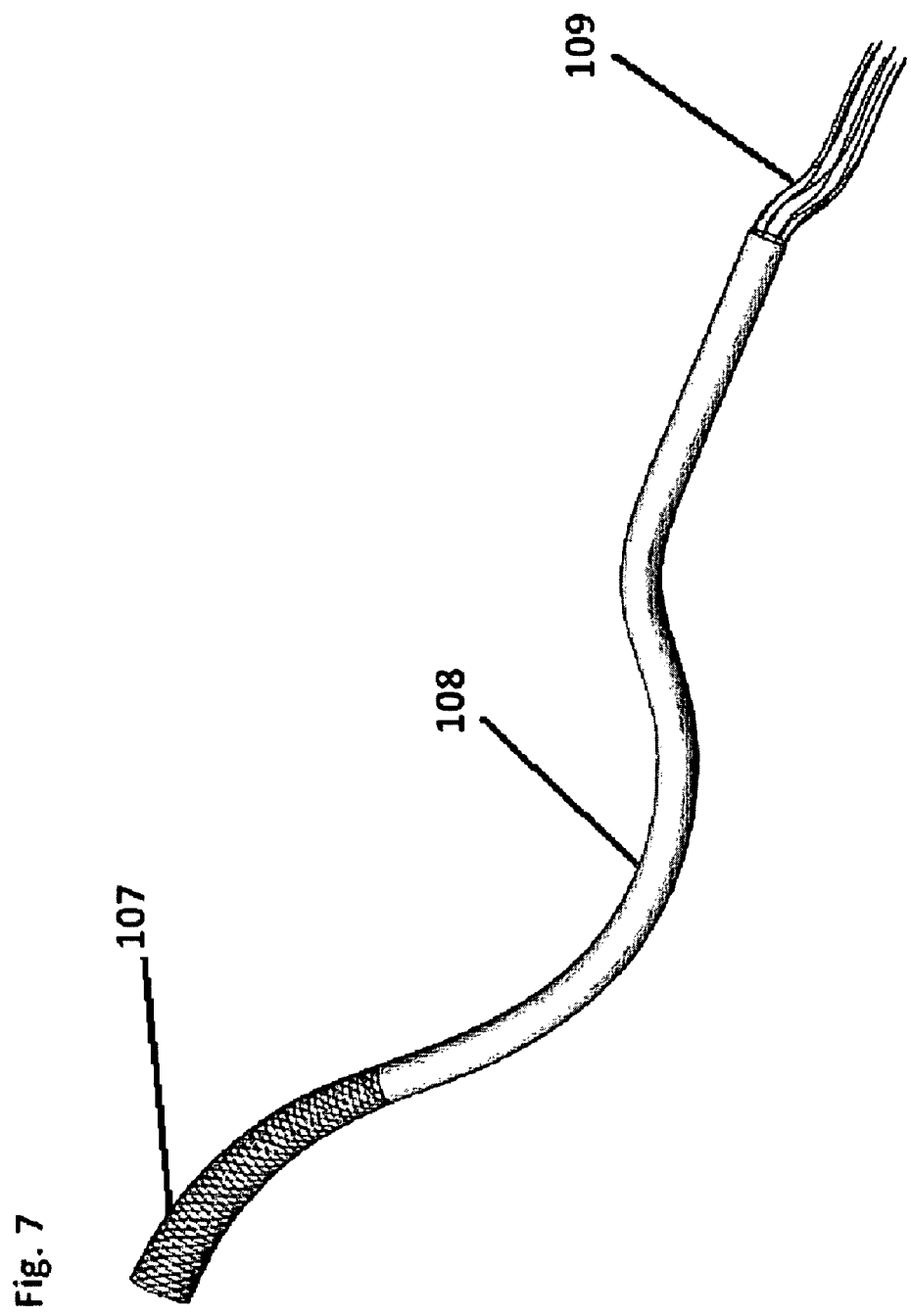
FIG. 7 shows the Urethral Sparing Prosthetic Stent (USPS) from the side illustrating the flexible curvature for conforming to a patient's anatomy with the stent at the upper left, the tubing in the center, and the retrieval strands in the lower right.
Figure 8:
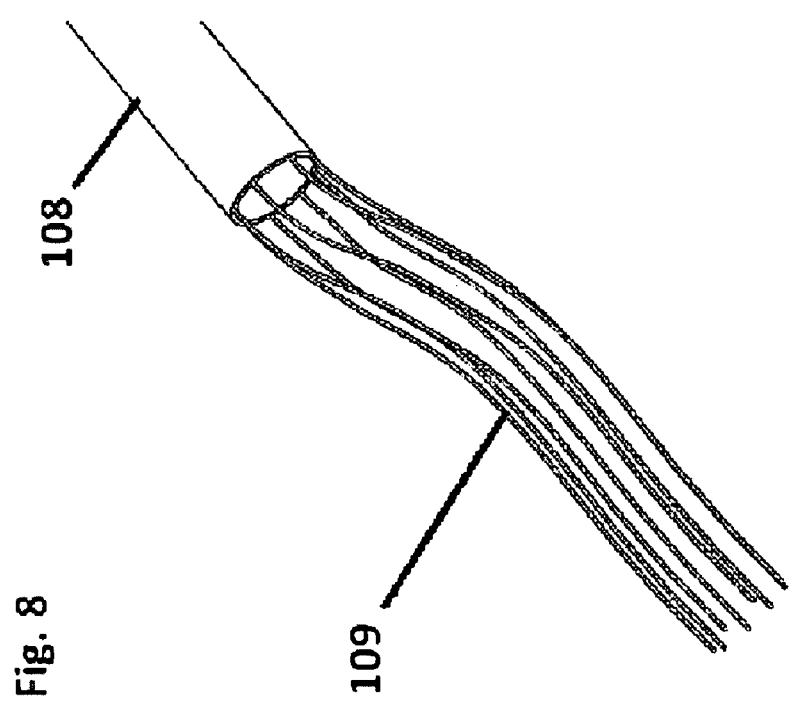
FIG. 8 shows the proximal end of the Urethral Sparing Prosthetic Stent (USPS) with the retrieval strands that exit the body at the left protruding from the tubing at the right.
Figure 9:
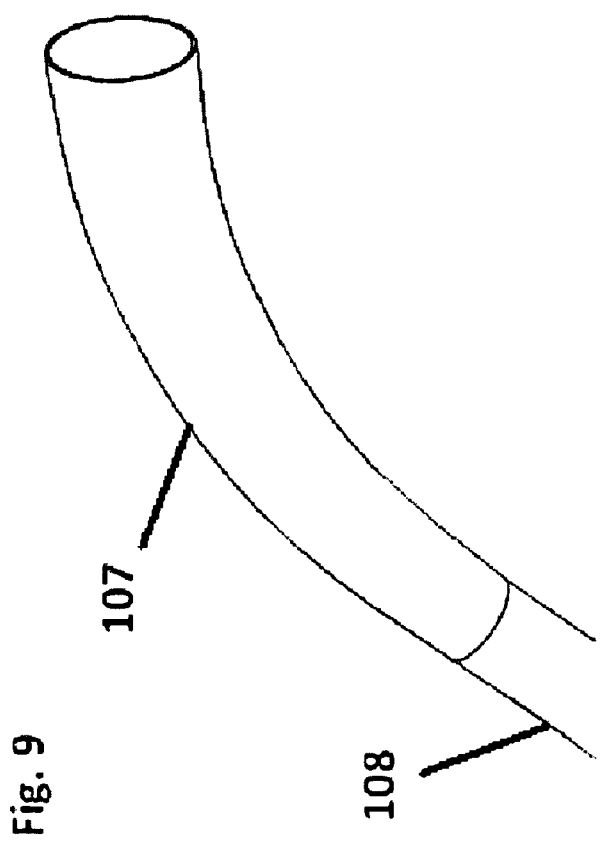
FIG. 9 shows the distal end of the Urethral Sparing Prosthetic Stent (USPS) with the stent at the right slightly expanded and closer to the distal end that enters the bladder and the tubing at the left narrower to pass through the urethra.
Figure 10:
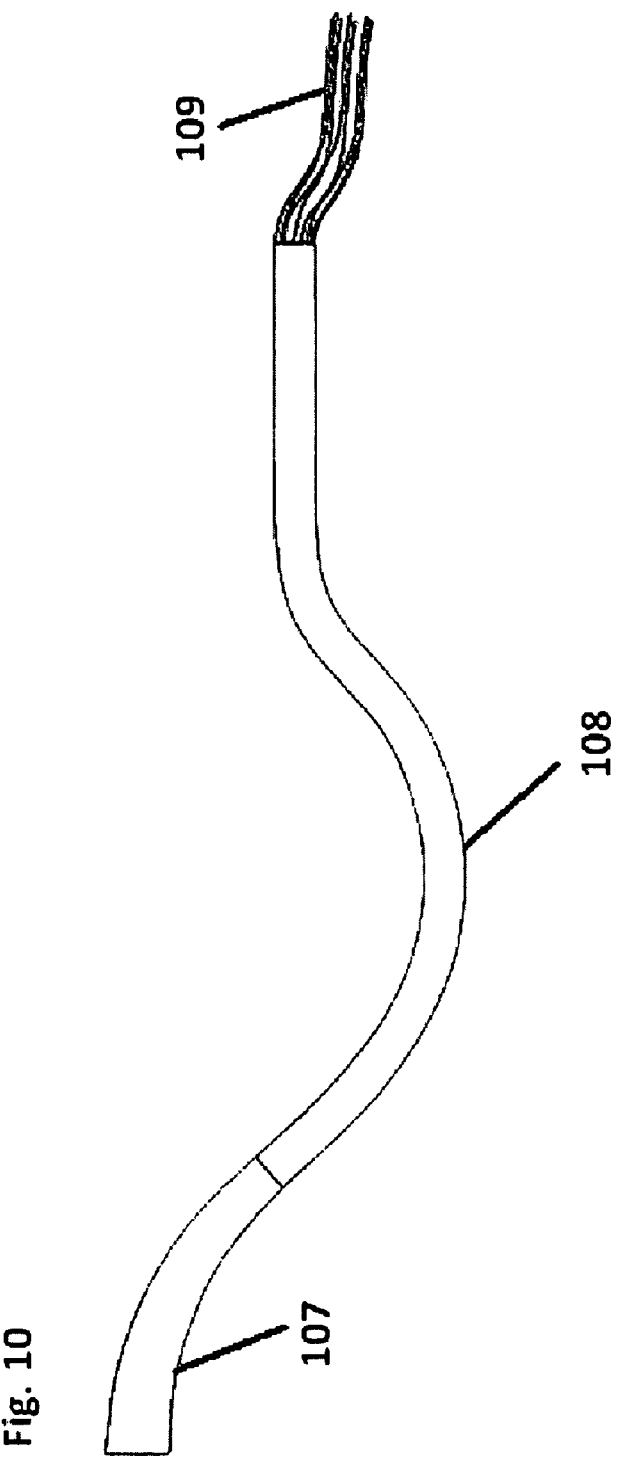
FIG. 10 shows a direct side view of the Urethral Sparing Prosthetic Stent (USPS) with the stent at the left, the tubing in the center, and the retrieval strands at the right.

FIGS. 7-10 show another component of the invention, the Urethral Sparing Prosthetic Stent (USPS). FIG. 7 and FIG. 10 show the entire USPS with the distal stent 107 configured to expand outward in diameter distally to provide a wider opening to receive stones in the bladder. The tubing 108 provides a smooth, atraumatic passage through the urethra for the stones that fall into the stent 107, and the strands 109 at the proximal end extend outside the body proximally and are attached to the distal stent 107 too. Pulling the strands 109 is the preferred means for retrieving the stent 107 causing it to collapsed inward into an optional retrieval balloon sheath (RBS) (not shown).

FIG. 8 shows only the proximal end of the USPS with the strands 109 extending from within the tubing 108 while FIG. 9 shows only the distal end of the USPS with the stent 107 that enters the bladder extending from the tubing 108. Any number of strands 109 may be provided, preferably four to eight.

From the above description of the invention, those skilled in the art will perceive improvements, changes and modifications. Such improvements, changes and modifications within the skill of the art are regarded as covered by the appended claims directly or as equivalents.

What is claimed is:

1. A urethral prosthetic for removing kidney stones, the urethral prosthetic comprising:
    a stent having a generally cylindrical shape and comprising a plurality of struts, a distal end and a proximal end, a distal section being biased to expand radially outward in a first configuration such that the distal end has an unobstructed flared opening configured to accept kidney stones and has a diameter that is greater than the diameter of the proximal end of the stent, and distal section being flexible so that it may to collapse radially in a second configuration such that the distal end has a diameter that is less than or equal to a diameter of the proximal end of the stent;
    a tubing attached to the stent, the tubing comprising an outer surface that is made of an atraumatic and biocompatible material;
    an inner surface that is made of a cushioned and lubricious material which defines an inner lumen of the tubing and has a length that is suitable to extend through an entire urethral canal from a bladder neck to a urethral exit of a patient's body; and
    a plurality of strands interwoven with the plurality of struts wherein each strand is intertwined with the plurality of struts, connects to the distal end of the stent, and extends along and is covered by the inner surface to emerge from a proximal end of the tubing such that pulling on proximal ends of the strands exerts a proximal pulling force on the distal end of the stent to collapse the stent from the first configuration to the second configuration.

2. The urethral prosthetic of claim 1 in combination with a balloon sheath that creates a channel when inflated, wherein the prosthetic is configured to be inserted inside the channel of the balloon sheath and delivered to or retrieved from the bladder neck.

3. The urethral prosthetic of claim 1, wherein at least one strand has a length greater than a length of the prosthetic such that the strand extends beyond the length of the prosthetic.

4. The urethral prosthetic of claim 1, wherein the outer surface comprises one or more of polytetrafluoroethylene (PTFE) and polyethylene terephthalate (PET).

5. The urethral prosthetic of claim 1, wherein the inner surface comprises one or more of polytetrafluoroethylene (PTFE) and polyethylene terephthalate (PET).

6. The urethral prosthetic of claim 1, wherein the outer surface extends over the stent.

7. The urethral prosthetic of claim 1, wherein the plurality of strands are made of nylon.

8. The urethral prosthetic of claim 1, wherein there are at least 4 strands and less than or equal to eight strands.

9. A urethral prosthetic of claim 1, wherein there are a sufficient number of strands to provide plurality of tensile angles on the distal end of the stent for an equal distributive pulling force.

10. A urethral prosthetic for removing kidney stones, comprising:
    a stent having a generally cylindrical shape and comprising a plurality of struts, a distal end and a proximal end, wherein a distal segment of the stent is biased to expand radially outward in a first configuration such that the distal end forms an unobstructed flared opening configured to accept kidney stones, the distal segment being adapted to collapse radially from the first configuration to a second configuration;
    a plurality of at least 4 strands interwoven with the plurality of struts, the strands being attached to the distal end of the stent and having a length longer than the stent so as to protrude beyond the proximal end of the stent; and
    a tubing covering the stent and the interwoven strands to prevent tissue from infiltrating the stent struts, the tubing extending along only a portion of the stent such that the distal end of the stent projects distally from a distal end of the tubing, the tubing being formed of an atraumatic, biocompatible and lubricious material and providing an external surface that protect the urethra;
    an inner smooth surface within the tubing defining an exit pathway for the kidney stones, the tubing and the inner surface having a length suitable to extend through an entire urethral canal from a bladder neck to a urethral exit, wherein the interwoven strands that protrude beyond the proximal end of the stent also protrude from a proximal end of the tubing and are covered by the inner surface to extend outside the body, wherein pulling the strands proximally collapses the stent from the first configuration to the second configuration.

11. A urethral prosthetic of claim 10, wherein there are a sufficient number of strands to provide plurality of tensile angles on the distal end of the stent for an equal distributive pulling force.

12. A urethral prosthetic of claim 11, wherein there are four to eight interwoven strands.

13. The urethral prosthetic of claim 10, in combination with a balloon sheath that creates a channel when inflated, wherein the prosthetic is configured to be inserted inside the channel of the balloon sheath and delivered to or retrieved from the bladder neck.

14. The urethral prosthetic of claim 10, wherein the tubing material comprises one or more of polytetrafluoroethylene (PTFE) and polyethylene terephthalate (PET).

15. The urethral prosthetic of claim 10, wherein the plurality of strands are made of nylon.

* * * * *